United States Patent [19]

Kelman

[11] Patent Number: 4,576,607
[45] Date of Patent: Mar. 18, 1986

[54] INTRAOCULAR LENSES

[76] Inventor: Charles D. Kelman, North Shore Towers - 269 Grand Central Pkwy., Bldg. 3, Floral Park, N.Y.

[21] Appl. No.: 630,695

[22] Filed: Jul. 13, 1984

[51] Int. Cl.⁴ ............................................... A61F 2/16
[52] U.S. Cl. .......................................................... 623/6
[58] Field of Search ............................................ 3/13, 1

[56] References Cited

U.S. PATENT DOCUMENTS

| 4,073,015 | 2/1978 | Peyman et al. | 3/13 |
| 4,253,200 | 3/1981 | Kelman | 3/13 |
| 4,403,353 | 9/1983 | Tennant | 3/13 |
| 4,468,820 | 9/1984 | Uhler et al. | 3/13 |

FOREIGN PATENT DOCUMENTS

| 2556665 | 6/1977 | Fed. Rep. of Germany | 3/13 |
| 2084024 | 4/1982 | United Kingdom | 3/13 |

Primary Examiner—Ronald L. Frinks
Attorney, Agent, or Firm—Henry Sternberg; Bert J. Lewen

[57] ABSTRACT

An intraocular lens with a medial light-focusing lens body includes oppositely disposed position fixation members having seating portions that are respectively resiliently retained between opposed groove portions of the eye. Each of the position fixation members is formed of at least two different materials for beneficial cooperation with the respective portions of the eye.

10 Claims, 4 Drawing Figures

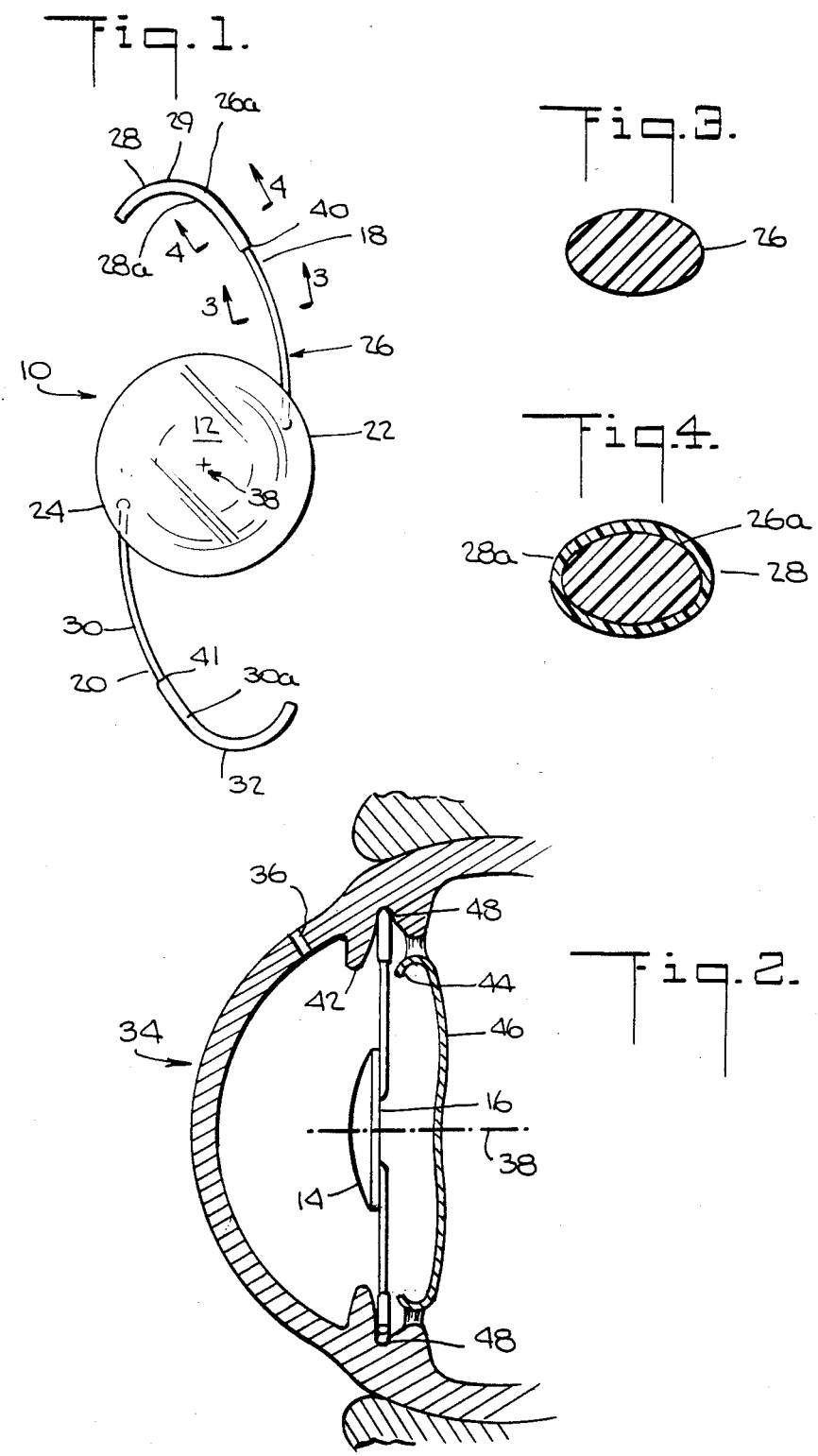

INTRAOCULAR LENSES

This invention relates to intraocular lenses for the human eye and more particularly to an intraocular lens having support members each comprising a plurality of different materials.

The insertion of an intraocular lens in the eye is a well known and widely used technique for restoring vision after a cataract removal operation. The natural structure of the eye furnishes a variety of locations for fixing the position of an introacular lens in the eye.

While it may be desirable to avoid more highly vascular regions by supporting the intraocular lens posteriorly of the iris in the cul-de-sac formed between the anterior and posterior capsule walls, such positioning cannot always be achieved because the extent of anterior wall structure at the upper portion of the eye that remains after cataract surgery is usually insufficient to accommodate and hold a position fixation member of the intraocular lens without suturing. Therefore, other locations in the eye which do not require sutures must be considered.

It has been found that a posterior chamber, two-loop intraocular lens such as described in my Pat. No. 4,253,200 can be implanted without sutures with one of its loops positioned superiorly in the upper groove formed by the ciliary sulcus of the eye between the iris and the anterior capsule wall and with the other of its loops positioned inferiorly in the lower groove formed within the capsule in the cul-de-sac between the posterior and the anterior capsule walls. It has also been suggested in my aforesaid patent that opposed position fixation members may each be formed of a different material for providing each with a different springiness so as to compensate for the different distances from the optical axis of the eye to the ciliary sulcus, on the one side, and to the cul-de-sac, on the other side.

Posterior chamber, two-loop intraocular lenses are also known which comprise a medial light-focusing lens body with a pair of oppositely disposed, dimensionally equivalent, position fixation members in the general shape of a "J". The J-shaped position fixation members are usually formed of polypropylene for sufficient spring-like quality to provide a soft resilient seating of the lens body in the ciliary sulcus of the eye. Although such soft resilient contact of the position fixation members provides stable positioning of the lens body in the eye without sutures, several problems may be encountered with such lenses made entirely of polypropylene. For example, it is my belief that polypropylene is not sufficiently inert and consequently causes irritation to the vascular tissue of the ciliary sulcus and resultant adhesion of such tissue to the position fixation member which is seated in the ciliary sulcus. Such adhesion could result in substantial difficulties if it were desired to remove the lens at a later date. On the other hand, known intraocular lenses having both their position fixation members of polymethylmethacrylate are much stiffer than polypropylene lenses and therefore a lens with two polymethylmethacrylate legs will tend to exert excessive pressure on the ciliary sulcus resulting in irritation of that region.

Among the several objects of the present invention may be noted the provision of an intraocular lens adapted to be resiliently retained in vascular tissue of the eye which, after implantation, does not exert excessive overall force on the vascular tissue, yet, which, I believe, is substantially less irritating and easier to remove from the eye, should such become desirable at some later date, than known, polypropylene lenses.

While there are known intraocular lenses having their position fixation members entirely of polymethylmethacrylate (PMMA) and there are known lenses having their position fixation members entirely of polypropylene, there have also been proposed intraocular lenses which have one position fixation member entirely of PMMA and the other position fixation member entirely of polypropylene. Each of these lens types has specific advantages and disadvantages when used in the eye. The intraocular lens according to the present invention combines these materials in a novel manner so as to derive the most advantageous characteristics of each.

The invention accordingly comprises the constructions hereinafter described, the scope of the invention being indicated in the following claims.

In the accompanying drawing in which the preferred embodiment of the invention is illustrated:

FIG. 1 is a simplified plan view of an intraocular lens according to the preferred embodiment of the present invention;

FIG. 2 is a simplified schematic sectional view of an eyeball with the intraocular lens seated therein;

FIG. 3 is a transverse sectional view taken in the direction of arrows 3—3 in FIG. 1; and FIG. 4 is a transverse sectional view taken in the direction of arrows 4—4 in FIG. 1.

Referring now to the drawing, an intraocular lens according to the preferred embodiment of the invention is generally indicated by reference numeral 10 in FIG. 1.

The intraocular lens includes a medial, light-focusing, lens body 12 intended to be positioned adjacent to the pupil in the anterior or posterior chamber having a convex or flat anterior surface 14 and a generally flat, or convex, posterior surface 16. A pair of position fixation members 18 and 20 are integrally joined to opposite peripheral sections 22 and 24 of the lens body 12.

The position fixation members 18 and 20 are preferably of J-shaped configuration. Position fixation member 18 has a leg portion 26 which extends from the peripheral section 22 to one end 40 of a curved seating portion 28 while position fixation member 20 has a leg portion 30 which extends from the peripheral section 24 to one end 41 of a curved seating portion 32.

The lens body 12 is formed of any suitable material which is compatible with the environment at the interior of the eyeball, such as a non-toxic plastic, as for example, polymethylmethacrylate. In the preferred form of the invention, seating portions 28 and 32 of position fixation members 18 and 20 are also formed of polymethylmethacrylate while leg portions 26 and 30 are formed of polypropylene, as will be described in more detail below.

Referring to FIG. 2, the intraocular lens 10 is inserted in an eyeball 34 using suitable known medical procedures, which include, for example, a corneo-scleral incision 36.

The lens body 12 has an optical axis 38, which is presumed to be the geometric center of the lens body. The eyeball 34 includes an anterior capsule wall 44 that has been partially removed with the cataract as shown in FIG. 2, and a posterior capsule wall 46.

A ciliary sulcus portion 48 of the eye is defined between the iris 42 and the anterior capsule wall 44. The ciliary sulcus 48 extends as a circumferential groove at upper and lower portions of the eye when viewed in cross-section.

When the intraocular lens 10 is implanted in the eye, the seating portions 28 and 32 are deflected toward the optical axis 38 of the lens and resiliently bear against the opposite interior peripheral groove surfaces of the eye formed by the ciliary sulcus 48. The force imposed by opposite portions of the ciliary sulcus 48 on the respective seating portions 28 and 32 readily deflect the more springy leg portions 26 and 30 so that the seating portions 28, 32 can both be disposed in the ciliary sulcus 48 without injury thereto.

This invention contemplates the use of different materials for the leg and the seating portions, respectively, of the position fixation members, wherein one material, while stiffer than the other has substantially better biological properties than the less stiff material. Specifically, the invention contemplates the use of polymethylmethacrylate for the seating portions of the position fixation members and polypropylene for the leg portions of the position fixation members. In accordance with the invention these materials are used in such a manner that the characteristics exhibited by each are used to full advantage as will now be described in more detail.

The polypropylene material of the leg portions 26 and 30 has the following characteristics as compared with the polymethylmethacrylate material of the seating portions 28 and 32:

(i) Polypropylene is, I believe, not nearly as inert as polymethylmethacrylate, which latter is substantially inert, i.e., causes practically no inflammatory reaction in adjacent living tissue and has substantially less tendency than polypropylene to adhere to living tissue. For example, many thousands of anterior chamber lenses made entirely of polymethylmethacrylate, with which there has been long term experience, exhibited little or no tendency to adhere to tissue. Polypropylene, sometimes referred to as Prolene, on the other hand, is attacked by the fluid in the eye and undergoes at least some changes in response thereto and to exposure to light, as a result of which polypropylene was found to develop tiny pits in which white blood cells can accumulate. The pitted polypropylene thus appears to form a matrix which facilitates rather than retards adhesion of adjacent tissue.

(ii) PMMA is much more rigid than Prolene, i.e., it is substantially less flexible than Prolene.

According to the present invention, the Prolene material is substantially out of contact with the vascular tissue of the eye, and only the PMMA material is allowed to contact the ciliary sulcus when the lens is implanted. In seating the lens, the seating portions 28, 32 of the position fixation elements, which in undeformed condition are preferably at least slightly spring further apart than the spacing between the grooves of the eye in which the lens is to be seated, must be deformed inwardly for proper seating. This also results in some pressure being exerted outwardly for maintaining the lens in proper position when the seating portions are properly seated in the ciliary sulcus. Since the Prolene leg portions are much more flexible than the PMMA seating portions, the Prolene leg portions will deform first and to a substantially greater amount than the PMMA seating portions.

While the capsular tissue is not living tissue, since it is not vascular tissue, the tissue in the ciliary sulcus, on the other hand, is living tissue. Even though the PMMA seating portions seated therein do not, due to the inert nature of the polymethylmethacrylate, adhere to the vascular tissue such as, I believe, it would, if the seating portions were formed of Prolene, as with prior lenses, nevertheless, if the pressure were sufficiently high, the PMMA seating portions would continue to press their way into the soft tissue of the ciliary sulcus and eventually that tissue would "grow around" those portions. This would create substantial problems, particularly if, at a later date, it were decided to remove the lens from the patient's eye. However, in accordance with the present invention, since the Prolene leg portions are substantially more flexible than would be leg portions of, for example, PMMA, i.e., exert substantially less spring pressure, the risk of tissue growing around the seating portion is much less than if the spring pressure were greater, as e.g. would be the case if the two position fixation members were formed exlcusively of PMMA. This facilitates removal of the lens at a later date, should such become necessary. The novel lens according to the present invention thus uses to optimum advantage the various physical characteristics exhibited by the materials Prolene and PMMA.

The dimensions of the various components of the intraocular lens 10 are substantially similar to those of the so called "Kratz Variation", Posterior Chamber, two loop intraocular lens made by Precision-Cosmet Co., Inc. Preferably, the cross sectional diameter of the leg portions 26, 30 is about 0.15 mm and the cross sectional diameter of the seating portions 28, 32 is about 0.20 mm.

It will be apparent from the foregoing that it is the specific nature and characteristics of the specific materials according to the present invention used in the particular way described above which results in the stated advantages.

As best seen in FIGS. 3 and 4, it is preferred to form the position fixation members 18 and 20 out of a Prolene filament which extends not only the length of leg portions 26, 30 but extends also the entire length of the seating portions 28, 32 respectively to the distal ends of the respective position fixation member. The seating portion 28 comprises a layer 28a of PMMA surrounding the inner filament 26a of Prolene which represents an extension of the filament 26 forming the leg portion. Preferably, the portion 28 will be of a length substantially equal to the length of the portion of the free end of the position fixation member which seats in and is in contact with the vascular tissue in the eye. The member 20 is preferably similarly constructed, with a sleeve-like layer of PMMA encapsulating the inner Prolene filament extension 30a of leg 30 from the end 41 to the distal end of member 30. It will be seen that the additional PMMA layer will reduce the flexibility of the seating portions 28, 32 in comparison with the leg portions 26, 30. It will also be understood that such layer of PMMA may be extruded about or otherwise applied around the filament portions 26a, 30a by known processes.

Alternatively, the seating portions 28, 32 may be formed entirely of PMMA and by known methods adhered (not shown) to the free ends of legs 26, 30, respectively, in the region 40, 41 respectively.

In view of the above, it will be seen that the several objects of the invention are achieved and other advantages results attained.

As various changes can be made in the above construction without departing from the scope of the invention, it is intended that all matter contained in the above description or shown in the accompanying drawing should be interpreted as illustrative and not in a limiting sense.

What is claimed is:

1. An intraocular lens suitable for use as an artifical lens implant, the lens comprising:
    a medial, light-focusing, lens body intended to be positioned adjacent to the pupil in the anterior or posterior chamber of the eye, and a pair of position fixation members connected with said lens body;
    one of the said position fixation members adapted to extend to and seat in the vascular tissue of a first groove portion of the eye adjacent ot the periphery of the iris;
    the other of said position fixation members adapted to extend to and seat in the vascular tissue of a second groove portion of the eye adjacent to the periphery of the iris;
    at least said one position fixation member comprising a resilient leg portion connected at one end with said lens body and a seating portion extending from the other end of said leg portion, said seating portion comprising a first material which is substantially biologically inert to the environment within the eye and exhibits a given springiness and said leg portion comprising a second material which is substantially less biologically inert to the environment within the eye than said first material and exhibits a substantially greater springiness than said first material.

2. The intraocular lens as claimed in claim 1, wherein said first material is polymethylmethacrylate and said second material is polypropylene.

3. The intraocular lens as claimed in claim 1 wherein said other of said position fixation elements comprises a leg portion connected at one end with said lens body and a seating portion extending from the other end of said leg portion, said seating portion comprising said first material and said leg portion comprising said second material.

4. The intraocular lens as claimed in claim 1 wherein said leg portion has an extension portion extending into said seating portion, said seating portion comprising a layer of said first material covering said extension portion of said leg portion.

5. The intraocular lens as claimed in claim 1 wherein said position fixation members are generally J-shaped filaments.

6. The intraocular lens as claimed in claim 1 wherein the length of said seating portion is determined by the length of the portion of said position fixation members which contacts tissue within the eye after the lens has been implanted therein.

7. The intraocular lens as claimed in claim 4 wherein said layer of first material is in the form of a sleeve surrounding said extension portion of said leg portion.

8. The intraocular lens as claimed in claim 4 wherein said extension portion is substantially coextensive with said seating portion.

9. The intraocular lens as claimed in claim 3 wherein said first material is polymethylmethacrylate, said second material is polypropylene, said seating portion comprises an inner filament of polypropylene surrounded by a sleeve of polymethylmethacrylate, and said filament forms an extension of said leg portion.

10. An intraocular lens suitable for use as an artificial lens implant, the lens comprising:
    a medial, light-focusing, lens body intended to be positioned adjacent to the pupil of the eye, and
    position fixation means integrally connected with said lens body said position fixation means including seating portions of polymethylmethacrylate spaced from said lens body for seating said lens in vascular tissue of the eye, and flexible leg portions of polypropylene filament intermediate said seating portion and said lens body for urging said seating portions outwardly into contact with said vascular tissue for seating the lens therein.

* * * * *